US00RE41393E

(19) United States
(12) Reissued Patent
Lee

(10) Patent Number: US RE41,393 E
(45) Date of Reissued Patent: Jun. 22, 2010

(54) TREATMENT OF REFRACTORY TUMORS USING EPOTHILONE DERIVATIVES

(75) Inventor: Francis Y.F. Lee, Yardley, PA (US)

(73) Assignee: Bristol-Myers Squibb Company, Princeton, NJ (US)

(21) Appl. No.: 11/346,579

(22) Filed: Feb. 2, 2006

Related U.S. Patent Documents

Reissue of:
(64) Patent No.: 6,686,380
Issued: Feb. 3, 2004
Appl. No.: 10/072,123
Filed: Feb. 8, 2002

U.S. Applications:
(60) Provisional application No. 60/269,836, filed on Feb. 20, 2001.

(51) Int. Cl.
*A61K 31/425* (2006.01)

(52) U.S. Cl. ..... 514/365; 514/183; 514/922
(58) Field of Classification Search ..... 514/183, 514/186, 365, 922
See application file for complete search history.

(56) References Cited

U.S. PATENT DOCUMENTS

| | | | | |
|---|---|---|---|---|
| 5,969,145 | A | 10/1999 | Schinzer et al. | 548/110 |
| 6,194,181 | B1 | 2/2001 | Hofmann et al. | |
| 6,204,388 | B1 | 3/2001 | Danishefsky et al. | |
| 6,211,412 | B1 | 4/2001 | Georg et al. | |
| 6,242,469 | B1 | 6/2001 | Danishefsky et al. | 514/365 |
| 6,262,094 | B1 | 7/2001 | Hoefle et al. | |
| 6,302,838 | B1 | 10/2001 | O'Reilly et al. | 514/365 |
| 6,316,630 | B1 | 11/2001 | Danishefsky et al. | |
| 6,365,749 | B1 | 4/2002 | Kim et al. | 548/205 |
| 6,369,234 | B1 | 4/2002 | Danishefsky et al. | |
| 6,518,421 | B1 | 2/2003 | Li et al. | 540/462 |
| 6,576,651 | B2 | 6/2003 | Bandyopadhyay et al. | 514/365 |
| 6,593,115 | B2 | 7/2003 | Vite et al. | 435/134 |
| 6,605,599 | B1 | 8/2003 | Vite et al. | 514/63 |
| 6,670,384 | B2 | 12/2003 | Bandyopadhyay et al. | 514/365 |
| 6,689,802 | B2 | 2/2004 | DiMarco et al. | 514/365 |
| 6,867,305 | B2 | 3/2005 | Danishefsky et al. | 548/204 |
| 6,982,276 | B2 | 1/2006 | DiMarco et al. | 514/365 |
| 2002/0010213 | A1 * | 1/2002 | Sawyer et al. | 514/568 |
| 2002/0143038 | A1 | 10/2002 | Bandyopadhyay et al. | 424/400 |
| 2002/0160354 | A1 * | 10/2002 | Cabot | 435/4 |

(Continued)

FOREIGN PATENT DOCUMENTS

| | | |
|---|---|---|
| DE | 4138042.8 | 5/1993 |
| DE | 19542986.9 | 5/1997 |
| DE | 19639456.2 | 5/1997 |
| DE | 19636343.8 | 3/1998 |
| DE | 19645361.5 | 4/1998 |
| DE | 19645362.3 | 4/1998 |
| DE | 19647580.5 | 5/1998 |
| DE | 19701758 | 7/1998 |
| DE | 19707505.3 | 9/1998 |
| DE | 19713970 | 10/1998 |
| DE | 19720312 | 11/1998 |
| DE | 19821954 | 11/1998 |
| DE | 19726627 | 12/1998 |
| EP | 879 605 | 11/1998 |
| WO | 93/10121 | 5/1993 |
| WO | 97/19086 | 5/1997 |
| WO | 98/08849 | 3/1998 |
| WO | 98/22461 | 5/1998 |
| WO | 98/24427 | 6/1998 |
| WO | 98/25929 | 6/1998 |
| WO | 98/38192 | 9/1998 |
| WO | 98/47891 | 10/1998 |
| WO | 99/01124 | 1/1999 |
| WO | 99/02514 | 1/1999 |
| WO | 99/03848 | 1/1999 |
| WO | 99/07692 | 2/1999 |
| WO | 99/27890 | 6/1999 |
| WO | 99/39694 | 8/1999 |
| WO | 99/42602 | 8/1999 |
| WO | 99/43320 | 9/1999 |
| WO | 99/43653 | 9/1999 |
| WO | 99/54319 | 10/1999 |
| WO | 99/67252 | 12/1999 |
| WO | 00/00485 | 1/2000 |
| WO | 00/31247 | 6/2000 |
| WO | 00/37473 | 6/2000 |
| WO | 00/49021 | 8/2000 |
| WO | WO 00/50423 | 8/2000 |
| WO | 00/68589 | 11/2000 |

OTHER PUBLICATIONS

U.S. Appl. No. 08/856,533 filed May 14, 1997, K. Nicolaou et al.

(Continued)

*Primary Examiner*—James D Anderson
(74) *Attorney, Agent, or Firm*—Anastasia P. Winslow

(57) ABSTRACT

Methods of treating tumors in a mammal, especially a human that has demonstrated resistance to other chemotherapeutic agents, is disclosed. Specifically, methods of the present invention are effective in tumors that have initially been unresponsive to taxane therapy, or have developed resistance during the course of treatment. The methods of the present invention comprise administering epothilone derivatives selected from those represented by the formula:

I

The subject epothilone derivatives are advantageous in addition to their enhanced potency and effectiveness against tumors that have demonstrated resistance to therapy with taxane oncology agents in that they are efficacious upon oral administration.

13 Claims, 3 Drawing Sheets

U.S. PATENT DOCUMENTS

| | | | | |
|---|---|---|---|---|
| 2002/0177615 | A1 | 11/2002 | Bandyopadhyay et al. | |
| 2003/0073677 | A1 | 4/2003 | Lee | 514/365 |
| 2004/0023345 | A1 | 2/2004 | Vite et al. | 435/134 |
| 2004/0024032 | A1 | 2/2004 | Voi et al. | 514/184 |
| 2004/0076177 | A1 | 4/2004 | Koch et al. | 370/465 |
| 2004/0132146 | A1 | 7/2004 | Benigini et al. | 435/119 |
| 2004/0214871 | A1 | 10/2004 | Lee | 514/365 |
| 2005/0159461 | A1 | 7/2005 | Lee | 514/365 |

OTHER PUBLICATIONS

U.S. Appl. No. 08/923,869 filed Sep. 4, 1997, K. Nicolaou et al.

U.S. Appl. No. 60/032,864 filed Dec. 13, 1996, K. Nicolaou et al.

Balog, A., et al., "Total Synthesis of (–)–Epothilone A", *Angew. Chem. Int. Ed. Eng.*, vol. 35, No. 23/24, 2801–2803 (1996).

Bertini, F., et al., "Alkenes from Epoxides by Reductive Elimination with Magnesium Bromide–Magnesium Amalgam", *Chem. Commun.*, 144 (1970).

Bollag, D.M., et al., "Epothilones, A New Class of Microtubule–stabilizing Agents with a Taxol–like Mechanism of Action", *Cancer Res.*55, No. 11, 2325–2333 (1995).

Fujisawa, T., et al., "Deoxygenation of Epoxides to Olefins with $FeCl_3$–n–BuLi System", *Chem. Lett.*, 883–886 (1974).

Fujiwara, Y., et al., "Reductive Coupling of Carbonyl Compounds to Olefins by Tungsten Hexachloride–Lithium Aluminum Hydride and Some Tungsten and Molybdenum Carbonyls", *J. Org. Chem.*, vol. 43, No. 12, 2477–2479 (1978).

Gladysz, J.A., et al., "Deoxygenation of Epoxides by Metal Atom Cocondensation", *J. Org. Chem.*, vol. 41, No. 22, 3647–3648 (1976).

Hoffe, G., et al., "Epothilone A and B—Novel 16—Membered Macrolides with Cytotoxic Activity: Isolation, Crystal Structure, and Conformation in Solution", *Angew. Chem. Int. Ed. Engl.*, vol. 35, No. 13/14, 1567–1569 (1996).

Hoffe, G., et al., "N–Oxidation of Epothilone A–C and O–Acyl Rearrangement to C–19 and C–21—Substituted Epothilones", *Angew. Chem. Int. Ed.*, vol. 38, No. 13/14, 1971–1974 (1999).

Inokuchi, T., et al., "Opening of Epoxides to Olefins or Halohydrins with Vanadium (ll)–Tetrahydrofuran or Vanadium (III)—Tetrahydrofuran Complexes", *Synlett*, No. 6, 510–512 (1992).

Kowalski, R. J., et al., "Activities of the Microtubule–stablizing Agents Epothilones A and B with Purified Tubulin and in Cells Resistant to Paclitaxel (Taxol®)" *J. Biol. Chem.*, vol. 272, No. 4, 2534–2541 (1997).

Kupchan, S. M., et al., "Reductive Elimination of Epoxides to Olefins with Zinc–Coppper Couple", *J. Org. Chem.*, vol. 36, No. 9, 1187–1190 (1971).

Martin, M. G., et al., "Epoxides as Alkene Protecting Groups. A Mild and Efficient Deoxygenation", *Tetrahedron Letters*, vol. 25, No. 3, 251–254 (1984).

McMurry, J. E., et al., "Reduction of Epoxides to Olefins with Low Valent Titanium", *J. Org. Chem.*, vol. 40, No. 17, 2555–2556 (1975).

McMurry, J.E., et al., "Some Deoxygenation Reactions with Low–Valent Titanium ($TiCL/LiAlH_4$ )", *J. Org. Chem.*, vol. 43, No. 17, 3249–3254.

Meng, D., et al., "Remote Effects in Macrolide Formation Through Ring–Forming Olefin Methathesis: An Application to the Synthesis of Fully Active Epothilone Congeners", *J. Am. Chem. Soc.*, vol. 119, No. 11, 2733–2734 (1997).

Nicolaou, K. C., et al., "An Approach to Epothilones Based on Olefin Metathesis", Angew. *Chem. Int. Ed. Engl.*, vol. 35, No. 20, 2399–2401(1996).

Nicolaou, K. C., et al., "Total Syntheses of Epothilone A: The Macrolactonization Approach", *Angew. Chem. Int. Engl.*, vol. 36, No. 5, 525–527 (1997).

Nicolaou, K. C., et al., "Designed Epothilones: Combinatorial Synthesis, Tubulin Assembly Properties, and Cytotoxic Action against Taxol–Resistant Tumor Cells", *Angew. Chem. Int. Ed. Engl.*, vol. 36, No. 19, 2097–2103 (1997).

Nicolaou, K.C., et al., "The Olefin Metathesis Approach to Epothilone A and Its Analogues", *J. Am. Chem. Soc.*, vol. 119, No. 34, 7960–7973 (1997).

Nicolaou, K.C., et al., "Total Synthesis of Epothilones A and B via a Macrolactonization–Based Strategy", *J. Am. Chem. Soc.*, vol. 119, No. 34, 7974–7991 (1997).

Nicolaou, K. C., et al., "Synthesis of Epothilones A and B in Solid and Solution Phase", *Nature*, vol. 387, 268–272 (1997).

Nicolaou, K. C., et al., "Synthesis of Epothilones A and B in Solid and Solution Phase" (Correction to Nature 387, 268–272 (1997)), *Nature*, 390, 100 (1997).

Raucher, S., et al., "Total Synthesis of (+)–Dihydrocostunolide via Tandem Cope–Claisen Rearrangement", *J. Org. Chem.*, vol. 51, No. 26, 5503–5505 (1986).

Sato, M, et al., "Reduction of Organic Compounds with Low–Valent Niobium ($NbCl_5/NaAlH_4$)", *Chem. Letters.*, 157–160 (1982).

Schinzer, D., et al., "Total Synthesis of (–)–Epothilone A", *Angew. Chem. Int. Ed. Engl.*, vol. 36, No. 5, 523–524 (1997).

Schobert, R., et al., "Reduction and Isomerization of Oxiranes and α–Diazoketones by Various Early Transition Metallocenes", Synlett, vol. 8, 465–466 (1990).

Sharpless, K.B., et al., "Lower Valent Tungsten Halides. A New Class of Reagents for Deoxygenation of Organic Molecules", *J. Amer. Chem. Soc.*, vol. 94, No. 18, 6538–6540 (1972).

Su, D.–S., et al., "Total Synthesis of (–)–Epothilone B: An Extension of the Suzuki Coupling Method and Insights into Structure–Activity Relationships of the Epothilones", *Angew. Chem. Int. Ed. Engl.*, vol. 36, No. 7, 757–759 (1997).

Su, D.–S., et al., "Structure–Activity Relationships of the Epothilones and the First In Vivo Comparison with Paclitaxel", *Angew. Chem. Int. Ed. Eng.l*, vol. 36, No. 19, 2093–2096 (1997).

Victory, S. F., et al., "Relative Stereochemistry and Solution Conformation of the Novel Paclitaxel–Like Antimitotic Agent Epothilone A", *Bioorg. Med. Chem. Letts.*, vol. 6, No. 7, 893–898 (1996).

Winkler, J. D., et al., "A Model For The Taxol (Paclitaxel) Epothilone Pharmacophore", *Bioorg. Med. Chem. Letters.*, vol. 6, No. 24, 2963–2966 (1966).

Yang, Z., et al., "Total Synthesis of Epothilone A: The Olefin Metathesis Approach", Angew. *Chem. Int. Ed. Engl.*, vol. 36, No. 1/2, 166–168 (1997).

Bollag, D., et al., "Epothilone, A New Structural Class of Microtubule Stabilizer", Abstract, *Proc. Am. Assoc. Cancer Res.*, vol. 36, 86 Meet. 454 (1995).

Bollag, D., "Epothilones: Novel Microtubule–Stabilising Agents", *Expert Opin. Invest. Drugs*, vol. 6, No. 7, 867–873 (1997).
Bertinato, P., et al., "Studies Toward a Synthesis of Epothilone A: Stereocontrolled Assembly of the Acyl Region and Models for Macrocyclization", J. Org. Chem., vol. 61, No. 23, 8000–8001 (1996).
*Chemical & Engineering News*, "Epothilone Epiphany: Total Synthesis", vol. 74, No. 52, 24–26 (1996).
*Chemical & Engineering News*, "First Total Synthesis of Epothilone B", vol. 75, No. 13, 23 (1997).
*Chemical & Engineering News*, "Solid–Phase Epothilone Synthesis Used to Create Analog Library", vol. 75, No. 20, 33 (1997).
Claus, E., et al., "Synthesis of the C1–C9 Segment of Epothilons", *Tetrahedron Lett.*, vol. 38, No. 8, 1359–1362 (1997).
De Brabander, J., et al., "Towards a Synthesis of Epothilone A: Rapid Assembly of the C1–C6 and C7–C12 Fragments", *Synlett*, vol. 7, 824–826 (1997).
Gabriel, T. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.*, vol. 38, No. 8, 1363–1366 (1997).
Gerth, K., et al., "Epothilons A and B: Antifungal and Cytotoxic Compounds from *Sorangiusm cellulosum*(Myxobacteria) Production, Physico–chemical and Biological Properties", *J. Antibiotics*, vol. 49, No. 6, 560–563 (1996).
Marshall, A., "Total Synthesis of Epothilone", *Nature Biotechnology*, vol. 15, No. 3, 205 (1997).
Meng, D., et al., "Studies Toward a Syntheses of Epothilone A: Use of Hydropyran Templates for the Management of Acyclic Stereochemical Relationships", *J. Org. Chem.*vol. 61, No. 23, 7998–7999 (1996).
Meng, D., et al., "Total Synthesis of Epothilones A and B", *J. Am. Chem. Soc.*, vol. 119, No. 42, 10073–10092 (1997).
Mensching, S. and Kalesse, M., "Generation of Thiazoles by Column Dehydrogenation of Thiazolidines with $MnO_2$", *J. Prakt. Chem.*, vol. 339, No. 1, 96–97 (1997).
Mulzer, J. and Mantoulidis, A., "Synthesis of the C(1)–C(9) Segment of the Cytotoxic Macrolides Epothilon A and B", *Tetrahedron Lett.*, vol. 37, No. 51, 9179–9182 (1996).
Nicolaou, K., et al., "Chemistry, Biology and Medicine of Selected Tubulin Polymerizing Agents", *Pure Appl. Chem.*, vol. 71, No. 6, 989–997 (1999).
Nicolaou, K., et al., "Total Synthesis of Epothilone E and Related Side–chain Modified Analogues Via a Stille Coupling Based Strategy", *Bioorg. Med. Chem.*, vol. 7, No. 5, 665–697 (1999).
Schinzer, D., et al., "Studies Towards the Total Synthesis of Epothilones: Asymmetric Synthesis of the Key Fragments", *Chem. Eur. J.*, vol. 2, No. 22, 1477–1482 (1996).
Taylor, R. and Haley, J., "Towards the Synthesis of Epothilone A: Enantioselective Preparation of the Thiazole Sidechain and Macrocyclic Ring Closure", *Tetrahedron Lett.*, vol. 38, No. 12, 2061–2064 (1997).
Schinzer, D., et al., "Syntheses of (13)–Epothilone A", *Chem. Eur. J.*, vol. 5, No. 9, 2483–2491 (1999).
Schinzer, D., et al., "Synthesis of (—)–Epothilone B", *Chem. Eur. J.*, vol. 5, No. 9, 2492–2500 (1999).
Nicolaou, K. C., et al., "Synthesis and Biological Properties of C12, 13–Cycloprpylpeothilone A and Related Epothilones", *Chemistry & Biology*, vol. 5, No. 7, 365–372 (1998).
Altmann, K.H., et al., "Epothilones and Related Structures—A New Class of Microtubule Inhibitors With Patent In Vivo Antitumor Activity", Biochim. Biophys Acta, 1470 (2000).
Nicolaou et al., "Total Synthesis of Epothilone E and Analogs with Modified Side Chains Through The Stille Coupling Reaction", Angew. Chem. Int. Ed. 37, 84–87 (1998).
Nicolaou et al., "Total Synthesis of Oxazole–and Cyclopropane–Containing Epothilone B Analogues by the Macrolactorization Approach", Chemistry, European Journal, vol. 3, No. 12, 1971–1986 (1997).
Nicolaou et al., "Chemical Biology of Epothilones", Angew. Chem. Int. Ed., 37, 2014–2045 (1988).
Chou et al., 1998, Desoxyepothilone B is curative against human tumor xenografts that are refractory to paclitaxel, Proc. Natl. Acad. Sci. USA 95: 15798–15802.
Borzilleri, R. M., et al., J. Am.Chem. Soc., vol. 122, 2000, pp. 8890–8897.
Blagosklonny, M.V., Leukemia, vol. 13, 1999, pp. 2031–2035.
Lee, F.Y.F. et al., Clinical Caner Research, vol. 7, May 2001 (May 2001) pp. 1429–1437.
Altman, K. H., "Synthesis and Biological Evaluation of Highly Potent Analogues or Epothilones B and D", Bioorganic & Med. Chem. Ltrs. 10 (2000), pp. 2765–2768.
Nicolaou, K.C., "Chemical Synthesis and Biological Properties of Pyridine Epothilones", Chemistry & Biology, vol. 7, No. 8, (2000) pp. 593–599.
Chou, T., et al., "Desoxyepothilone B: An Efficacious Microtubule—targeted Antitumor Agent with a Promising In Vivo Profile Relative to Epothilone B" PNAS, vol. 95, Aug. 1998, pp. 9642–9647.
Gerth, et al. "Studies on the Biosynthesis of Epothilones: The Biosynthetic Origin of the Carbon Skelton", Journal of Antibiotics, vol. 53, No. 12, Dec. 2000, pp. 1373–1377.
Danishefsky et al. "Remote Effects in Macrolide Formation through Ring–Forming Olefin Metathesis: An Application to the Synthesis of Fully Active Epothilone Congeners", J. Am. Chem. Soc., vol. 119, (1997) pp. 2733–2734.
Hardt, et al., "New Natural Epothilones from Sorangium cellulosum, Strains So ce90/B2 and So ce90/D13: Isolation, Structure Elucidation and SAR Studies", J. of Natural Products, vol. 64, No. 7, (2001) pp. 847–856.
Abstract and Slides: Lee, Francis, et al., "An Epothilone Analog Possessing Potent Activity Against Paclitaxel Sensitive and Resistant Human Tumors", Proceedings of the American Association for Cancer Research, 91$^{st}$Ann. Meeting. San Francisco, CA, Apr. 1–5, 2000.
U.S. Appl. No. 60/032,864, Nicolaou et al., filed Dec. 13, 1996.

* cited by examiner

| BMS-247550 | |
|---|---|
| Cell Line | $IC_{50}$ (μM) |
| A2780/DDP-S | 0.0028 |
| A2780/DDP-R | 0.0018 |
| A2780/TAX-S | 0.0026 |
| A2780/TAX-R | 0.0049 |
| OVCAR-3 | 0.0018 |
| MCF-7 | 0.0027 |
| SKBR3 | 0.0023 |
| LNCAP | 0.0015 |
| PC3 | 0.0046 |
| HCT116 | 0.0026 |
| HCT116/VM46 | 0.0245 |
| HCT116/VP35 | 0.0020 |
| LS174T | 0.0058 |
| MIP | 0.0248 |
| CACO-2 | ND |
| A549 | 0.0052 |
| LX-1 | 0.0031 |
| A431 | 0.0014 |
| CCRF-CEM | 0.0060 |
| HL60 | ND |
| K562 | 0.0029 |
| ABAE | ND |
| HS27 | ND |
| M109 | 0.0029 |
| MLF | 0.0345 |
| Median IC50 | 0.0029 |
| GeoMean IC50 | 0.0039 |
| Min IC50 | 0.0014 |
| Max IC50 | 0.0345 |
| Range(LogIC50) | 1.41 |

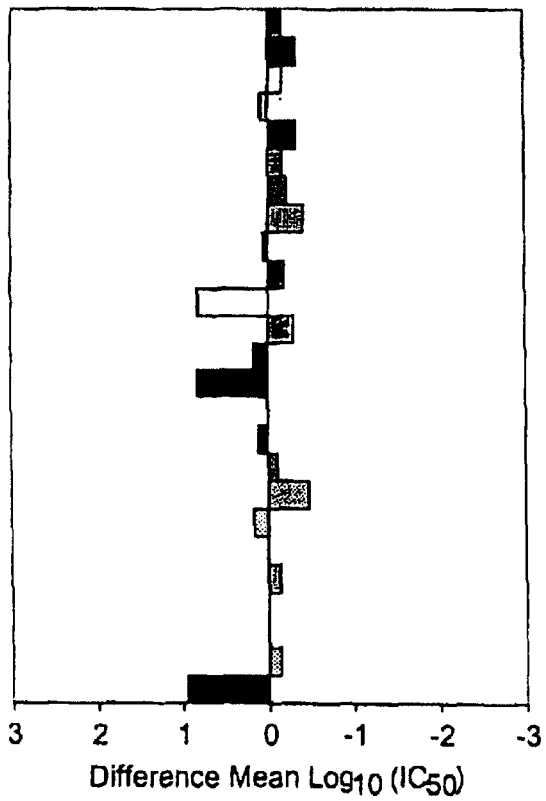

Figure 1. Cytotoxicity spectrum of BMS-247550 versus a panel of tumor cell lines. The mean bar graph, on the right, graphically depicts the difference between the log of the individual cell line $IC_{50}$ values relative to the mean log of all the $IC_{50}$ values. Right projecting bars indicate sensitive cells and left projecting bars indicate resistant cell lines. Mean $IC_{50}$ = 3.9 nM. ND= Not done.

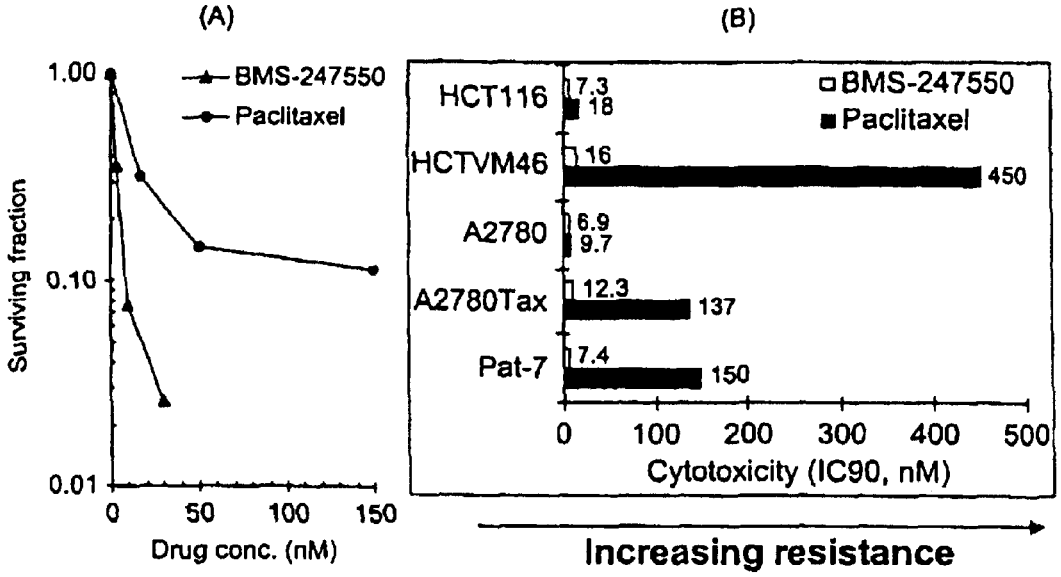

Figure 2. BMS-247550 retains its anticancer cytotoxicity against tumor types that had developed resistance to paclitaxel. (A) Clonogenic cell survival of Pat-7 ovarian carcinoma cells following a 16 hr exposure to BMS-247550 or paclitaxel. (B) Comparative cytotoxic potency ($IC_{90}$) of BMS-247550 and paclitaxel in five human tumor lines: HCT116 human colon carcinoma; HCT116/VM46 (MDR-resistant variant derived from HCT116); A2780 human ovarian ca.; A2780Tax (paclitaxel-resistant variant due to a mutation in beta-tubulin; Pat-7 human ovarian ca. (derived from a patient who had developed resistance to Taxol® monotherapy). $IC_{90}$'s are the concentration of the agent required to reduce colony formation by 90%. $IC_{90}$ values are shown next to the bar graphs.

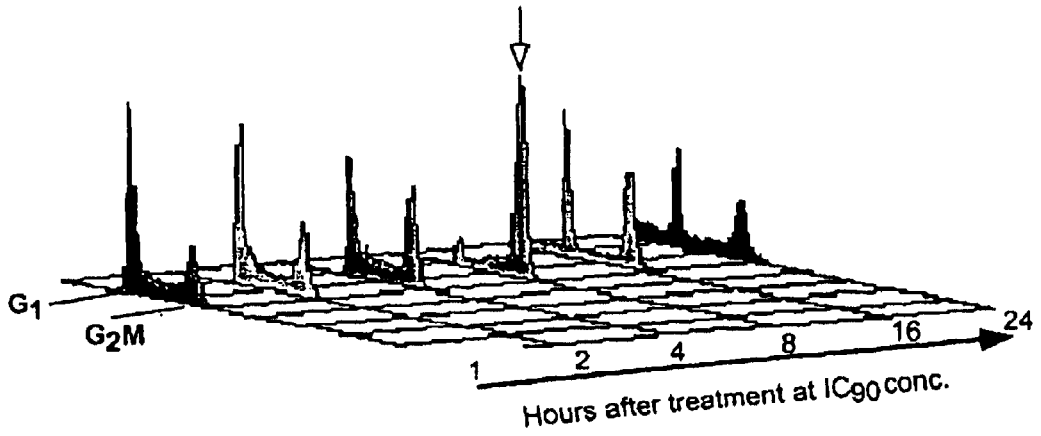
Figure 3. Time-course of the mitotic blockade induced by the incubation of HCT116 colon carcinoma cells in cell culture media containing 7.5 nM ($IC_{90}$) BMS-247550. The arrow indicates the position of the $G_2M$ cell population.

TREATMENT OF REFRACTORY TUMORS USING EPOTHILONE DERIVATIVES

Matter enclosed in heavy brackets [ ] appears in the original patent but forms no part of this reissue specification; matter printed in italics indicates the additions made by reissue.

CROSS-REFERENCE TO RELATED APPLICATIONS

This application claims priority from provisional application serial No. 60/269,836, filed Feb. 20, 2001, incorporated herein by reference in its entirety.

FIELD OF THE INVENTION

The present invention relates to the use of certain potent epothilone analogs in the treatment of tumors that have demonstrated resistance to therapy with other chemotherapeutic agents.

BACKGROUND OF THE INVENTION

Epothiolones are macrolide compounds that find utility in the pharmaceutical field. For example, epothilones A and B having the structures:

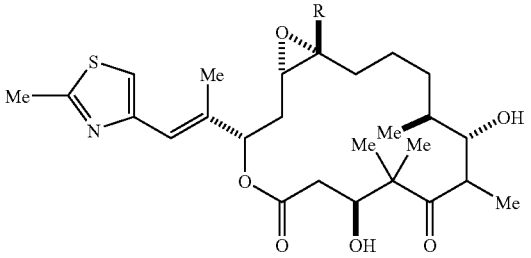

Epothilone A
R = H

Epothilone B
R = Me may be found to exert microtubule-stabilizing effects similar to paclitaxel (TAXOL®) and hence cytotoxic activity against rapidly proliferating cells, such as tumor cells or other hyperproliferative cellular diseases. See, Hofle et al., Angew. Chem. Int. Ed. Engl., Vol. 35, No. 13/14, 1567–1569 (1996); WO93/10121 published May 27, 1993; and WO97/19086 published May 29, 1997.

Derivatives and analogs of epothilones A and B have been synthesized and may be used to treat a variety of cancers and other abnormal proliferative diseases. Such analogs are disclosed in Hofle et al., Id.; Nicolaou et al., Agnew. Chem. Int. Ed. Eng., Vol.36, No. 19, 2097–2103 (1997); and Su et al., Agnew. Chem. Int. Ed. Engl., Vol. 36, No. 19, 2093–2097 (1997). In some instances, epothilone derivatives have demonstrated enhanced properties over epothilones A and B. The present invention is concerned with the discovery that certain epothilone derivatives may be utilized to treat cancers that have demonstrated resistance to other chemotherapeutic agents, such as oncolytic agents of the taxane family of compounds.

SUMMARY OF THE INVENTION

In accordance with the present invention, tumors demonstrating a clinical resistance to treatment with other chemotherapeutic agents, such as taxane oncolytic agents, may be treated with an epothilone derivative selected from those represented by formula I:

I

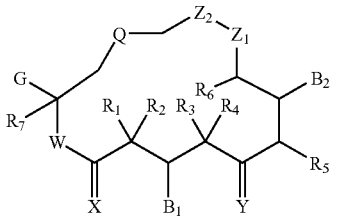

wherein $B_1$, $B_2$, G, Q, X, Y, $Z_1$, $Z_2$, and $R_1$ through $R_7$ have the meanings given below. The compounds represented by formula I have previously demonstrated significantly enhanced potency over known chemotherapeutic agents, for example, epothilones A and B above and certain others including those in the taxane series. Compounds represented by formula I are further advantageous in that, unlike most oncology agents, they are efficacious via oral administration.

BRIEF DESCRIPTION OF THE DRAWINGS

FIG. 1 is a bar graph showing the cytotoxicity spectrum of a compound of the invention against a panel of tumor cell lines.

FIG. 2 is a bar graph showing the cytotoxicity of a compound of the invention against paclitaxel-resistant tumors.

FIG. 3 shows the mitotic blockade induced by a compound of the invention.

DETAILED DESCRIPTION OF THE INVENTION

Processes of the present invention provide advantageous treatment for tumors that have demonstrated resistance to treatment with chemotherapeutic agents, such as those of the taxane family. The term "resistance to treatment" as utilized herein includes both tumors that are initially unresponsive to treatment with a chemotherapeutic agent as well as tumors that are initially responsive, but develop resistance over the course of treatment. Compounds useful in the subject method are epothilones, a class of oncology chemotherapeutic agents chemically distinct from the taxane family of oncology agents. The subject epothilone derivatives are represented by formula I:

I

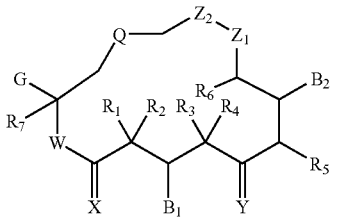

wherein

Q is selected from the group consisting of

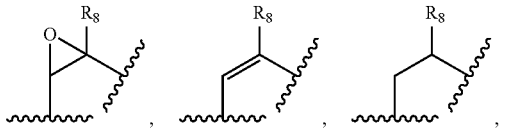

-continued

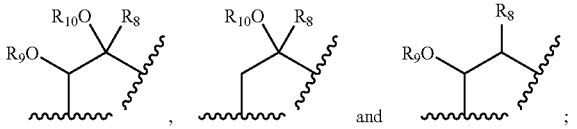

G is selected from the group consisting of alkyl, substituted alkyl, aryl, substituted aryl, heterocyclo,

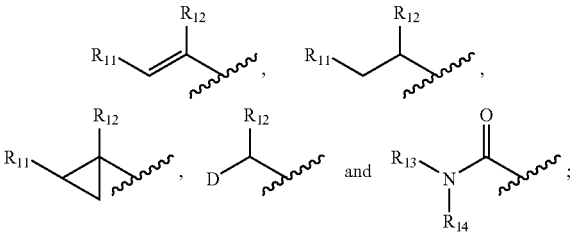

W is O or N $R_{15}$;

X is O or H, H;

Y is selected from the group consisting of O; H, $OR_{16}$; $OR_{17}$, $OR_{17}$; $NOR_{18}$; H, $NHOR_{19}$; H, $NR_{20}R_{21}$; H, H; and $CHR_{25}$; wherein $OR_{17}$, $OR_{17}$ can be cyclic ketal;

each $Z_1$ and $Z_2$ is, independently, selected from the group consisting of $CH_2$, O, $NR_{23}$, S, and $SO_2$, wherein only one of $Z_1$ and $Z_2$ can be a heteroatom;

each $B_1$ and $B_2$ is, independently, selected from the group consisting of $OR_{24}$, $OCOR_{25}$, and O—C(═O)—$NR_{26}R_{27}$, and when $B_1$ is H and Y is OH, H, they can form a six-membered ring ketal or acetal;

D is selected from the group consisting of $NR_{28}R_{29}$, $NR_{30}COR_{31}$ and saturated heterocycle;

each $R_1$, $R_2$, $R_3$, $R_4$, $R_5$, $R_6$, $R_7$, $R_{13}$, $R_{14}$, $R_{18}$, $R_{19}$, $R_{20}$, $R_{21}$, $R_{22}$, $R_{26}$ and $R_{27}$ is, independently, selected from the group consisting of H, alkyl, substituted alkyl, and aryl, and when $R_1$ and $R_2$ are alkyl they can be joined to form cycloalkyl, and when $R_3$ and $R_4$ are alkyl they can be joined to form cycloalkyl;

each $R_9$, $R_{10}$, $R_{16}$, $R_{17}$, $R_{24}$, $R_{25}$ and $R_{31}$ is, independently, selected from the group consisting of H, alkyl, and substituted alkyl;

each $R_8$, $R_{11}$, $R_{12}$, $R_{28}$, $R_{30}$, $R_{32}$, and $R_{33}$ is, independently, selected from the group consisting of H, alkyl, substituted alkyl, aryl, substituted aryl, cycloalkyl and heterocyclo; and each $R_{15}$, $R_{23}$ and $R_{29}$ is, independently, selected from the group consisting of H, alkyl, substituted alkyl, aryl, substituted aryl, cycloalkyl, heterocyclo, $R_{32}C$═O, $R_{33}SO_2$, hydroxy, O-alkyl or O-substituted alkyl;

and pharmaceutically acceptable salts thereof and any hydrates, solvates or geometric, optical and stereoisomers thereof, with the proviso that compounds wherein W and X are both O; $R_1$, $R_2$ and $R_7$ are H; $R_3$, $R_4$ and $R_6$ are methyl; $R_8$ is H or methyl; $Z_1$ and $Z_2$ are $CH_2$; G is 1-methyl-2-(substituted-4-thiazolyl)ethenyl; and Q is as defined above, are excluded.

Preferred compounds in accordance with the present invention are those represented by formula I above wherein Q is

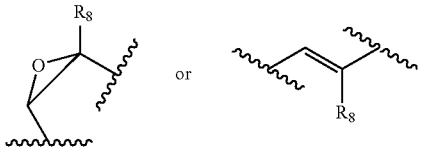

X is O; Y is O; $Z_1$ and $Z_2$ are $CH_2$; and W is $NR_{15}$.

Another preferred group of compounds in accordance with the present invention is represented below:

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4,13,17-trioxabicyclo[14.1.0]heptadecane-5,9-dione;

[1 S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-4,13,17-trioxabicyclo[14.1.0]heptadecane-5,9-dione;

[4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-1,10-dioxa-13-cyclohexadecene-2,6-dione;

[4S-[4R*,7S *,8R*,9R*,15R*(E)]]-4,8-dihydroxy-5,5,7,9-tetramethyl-16-[1-methyl-2-(2-methyl-4-thiazolyl)ethenyl]-1,10-dioxa-13-cyclohexadecene-2,6-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4,14,17-trioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-4,14,17-trioxabicyclo[14.1.0]heptadecane-5,9-dione;

[4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-1,11-dioxa-13-cyclohexadecene-2,6-dione;

[4S-[4R*,7S*,8R*,9R*,15R*(E)]]-4,8-dihydroxy-5,5,7,9-tetramethyl-16-[1-methyl-2-(2-methyl-4-thiazolyl)ethenyl]-1,11-dioxa-13-cyclohexadecene-2,6-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4,17-dioxabicyclo[14.1.0]heptadecane-9-one;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-4,17-dioxabicyclo[14.1.0]heptadecane-9-one; hexamethyl-3-[1-methyl-2-(2-methyl-4-thiazolyl)ethenyl]-4, 17-dioxabicyclo[14.1.0]heptadecane-5,9-dione;

[1S-[1R*,3R*(E),7R*,10S*,11R*,12R*,16S*]]-7,11-dihydroxy-3,8,8,10,12-pentamethyl-3-[1-methyl-2-(2-methyl-4-thiazolyl)ethenyl]-4,17-dioxabicyclo[14.1.0]heptadecane-5,9-dione;

[4S-[4R*,7S*,8R*,9R*,15R*(E)]]-4,8-dihydroxy-5,5,7,9,13,16-hexamethyl-16-[1-methyl-2-(2-methyl-4-thiazolyl)ethenyl]-1-oxa-13-cyclohexadecene-2,6-dione;

[4S-[4R*,7S*,8R*,9R*,15R*(E)]]-4,8-dihydroxy-5,5,7,9,16-pentamethyl-16-[1-methyl-2-(2-methyl-4-thiazolyl)ethenyl]-1-oxa-13-cyclohexadecene-2,6-dione;

[1 S-[R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4,17-dioxabicyclo[14.1.0]heptadecane-5,9-dione;

[1S-[1R*,3R*(E),7R*,10S*,11 R*,12R*,16S*]]-7,11-dihydroxy-6,8,8,10,12-pentamethyl-3-[1-methyl-2-(2-methyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione;

[1 S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-4-aza-17-oxabicyclo[14.1.0]heptadecane-5,9-dione;

[4S-[4R*,7S *,8R*,9R*,15R*(E)]]-4,8-dihydroxy-5,5,7,9,13-pentamethyl-16-[1-methyl-2-(2-methyl-4-thiazolyl)ethenyl]-1-aza-13-cyclohexadecene-2,6-dione;

[4S-[4R*,7S*,8R*,9R*,15R*(E)]]-4,8-dihydroxy-5,5,7,9-tetramethyl-16-[1-methyl-2-(2-methyl-4-thiazolyl)ethenyl]-1-aza-13-cyclohexadecene-2,6-dione;

[1S-[1R*,3R*(E),7R*,10S*,11R*,12R*,16S*]]-7,11-dihydroxy-4,8,8,10,12,16-hexamethyl-3-[1-methyl-2-(2-methyl-4-thiazolyl)ethenyl]-4-aza-17-oxabicyclo[14.1.0]heptadecane-5,9-dione;

[1S-[R*,3R*(E),7R*,10S*,11R*,12R*,16S*]]-7,11-dihydroxy-4,8,8,10,12-pentamethyl-3-[1-methyl-2-(2-methyl-4-thiazolyl)ethenyl]-4-aza-17-oxabicyclo[14.1.0]heptadecane-5,9-dione;

[4S-[4R*,7S*,8R*,9 R*,15R*(E)4,8-dihydroxy-1,5,5,7,9,13-hexamethyl-16-[1-methyl-2-(2-methyl-4-thiazolyl)ethenyl]-1-aza-13-cyclohexadecene-2,6-dione;

[4S-[4R*,7S*,8R*,9R*,15R*(E)]]-4,8-dihydroxy-1,5,5,7,9-pentamethyl-16-[1-methyl-2-(2-methyl-4-thiazolyl)ethenyl]-1-aza-13-cyclohexadecene-2,6-dione;

[1S-[1R*,3R*(E),7R*,10S*,11R*,12R*,16S*]]-7,11-dihdyroxy-8,8,10,12,16-pentamethyl-3-[1-methyl-2-(2-methyl-4-thiazolyl)ethenyl]-13-aza-4,17-dioxabicyclo[14.1.0]heptadecane-5,9-dione;

[1 S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-13-aza-4,17dioxabicyclo[14.1.0]heptadecane-5,9-dione;

[4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-10-aza-1-oxa-13-cyclohexadecene-2,6-dione;

[4S-[4R*,7S*,8R*,9R*,15R*(E)]]-4,8-dihydroxy-5,5,7,9-tetramethyl-16-[1-methyl-2-(2-methyl-4-thiazolyl)ethenyl]-10-aza-1-oxa-13-cyclohexadecene-2,6-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-14-aza-4,17-dioxabicyclo[14.1.0]heptadecane-5,9-dione;

[1S-[R*,3R*(E),7R*,10S*,11R*,12R*,16S* ]]-7,11-dihydroxy-8,8,10,12-tetramethyl-3-[1-methyl-2-(2-methyl-4-thiazolyl)ethenyl]-14-aza-4,17-dioxabicyclo[14.1.0]heptadecane-5,9-dione;

[4S-[4R*,7S,8R*,9R*,15R*(E)]]-4,8-dihydroxy-5,5,7,9,13-pentamethyl-16-[1-methyl-2-(2-methyl-4-triazolyl)ethenyl]-11-aza-1-oxa-13-cyclohexadecene-2,6-dione;

[4S-[4R*,7S*,8R*,9R*15R*(E)]]-4,8-dihydroxy-5,5,7,9-tetramethyl-16-[1-methyl-2-(2-methyl-4-thiazolyl)ethenyl]-11-aza-1-oxa-13-cyclohexadecene-2,6-dione;

[1 S-[1R*,3R*,7R*,10S*,11R*,12R*,16S*]]-N-phenyl-7,11-dihydroxy-8,8,10,12,16-pentamethyl-5,9-dioxo-4,17-dioxabicyclo[14.1.0]heptadecane-3-carboxamide;

[1S-[1R*,3R*,7R*,10S*,11R*,12R*,16S*]]-N-phenyl-7,11-dihydroxy-8,8,10,12-tetramethyl-5,9-dioxo-4,17-dioxabicyclo[14.1.0]heptadecane-3-carboxamide;

4S-[4R*,7S *,8R*,9R*,15R*]]-N-phenyl-4,8-dihydroxy-5,5,7,9,13-pentamethyl-2,6-dioxo-1-oxa-13-cyclohexadecene-16-carboxamide;

[4S-[4R*,7S,8R*,9R*,15R*]]-N-phenyl-4,8-dihydroxy-5,5,7,9-tetramethyl-2,6-dioxo-1-oxa-13-cyclohexadecene-16-carboxamide;

[1S-1R*,3R*(E),7R*,10S*,11R*,12R*,16S*]]-7,11-dihydroxy-8,8,10,12,16-pentamethyl-3-[1-methyl-2-(2-methyl-4-thiazolyl)cyclopropyl]-4,17-dioxabicyclo[14.1.0]heptadecane-5,9-dione;

1[S-[1R*,3R*(E),7R*,10S*,11R, 12R*,16S*]]-7,11-dihydroxy-8,8,10,12-tetramethyl-3-[1-methyl-2-(2-methyl-4-thiazolyl)cyclopropyl]-4,17-dioxabicyclo[14.1.0]heptadecane-5,9-dione; and

[4S-[4R*,7S*,8R*,9R*,15R*(E)]]-4,8-dihydroxy-5,5,7,9,13-pentamethyl-16-[1-methyl-2-(2-hydroxymethyl-4-thiazolyl)ethenyl]-1-aza-13(Z)-cyclohexadecene-2,6-dione;

and pharmaceutically acceptable salts, solvates and hydrates thereof.

A particular preferred compound in accordance with the present invention is represented by the formula:

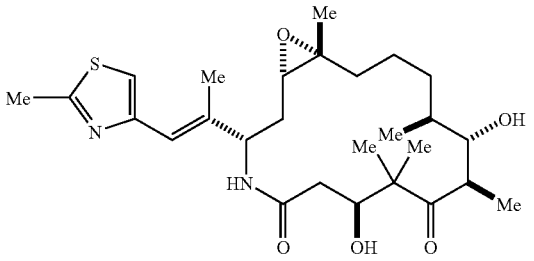

This compound chemically is [1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione.

The epothilone derivatives represented by formula I above and processes for their preparation are disclosed in WO 99/02514, WO 99/27890, WO 99/28324. Heretofore, however, there has been no recognition that the subject epothilone derivatives would possess activity in the treatment of tumors resistant to treatment with other known chemotherapeutic agents.

The following are definitions of various terms used to describe the compound represented by formula I above.

The term "alkyl" refers to optionally substituted straight- or branched-chain saturated hydrocarbon groups having from 1 to about 20 carbon atoms, preferably from 1 to about 7 carbon atoms. The expression "lower alkyl" refers to optionally substituted alkyl groups having from 1 to about 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryl, aryloxy, aralkyl, alkanoyloxy, amino, alkylamino, arylamino, aralkylamino, cycloalkylamino, heterocycloamino, disubstituted amino in which the two substituents on the amino group are selected from alkyl, aryl, aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g., $SO_2NH_2$), substituted sulfonamido, nitro, cyano, carboxy, carbamyl (e.g., $CONH_2$), substituted carbamyl (e.g., CONH alkyl, CONH aryl, CONH aralkyl or instances where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Wherein, as noted above, the substituents themselves are further substituted, such further substituents are selected from the group consisting of halogen, alkyl, alkoxy, aryl and aralkyl. The definitions given herein for alkyl and substituted alkyl apply as well to the alkyl portion of alkoxy groups.

The term "alkenyl" refers to optionally substituted unsaturated aliphatic hydrocarbon groups having from 1 to about 9 carbons and one or more double bonds. Substituents may include one or more substituent groups as described above for substituted alkyl.

The term "halogen" or "halo" refers to fluorine, chlorine, bromine and iodine.

The term "ring system" refers to an optionally substituted ring system containing one to three rings and at least one carbon to carbon double bond in at least one ring. Exemplary ring systems include, but are not limited to, an aryl or a partially or fully unsaturated heterocyclic ring system, which may be optionally substituted.

The term "aryl" refers to monocyclic or bicyclic aromatic hydrocarbon groups having from about 6 to about 12 carbon atoms in the ring portion, for example, phenyl, naphthyl, biphenyl and diphenyl groups, each of which may be substituted.

The term "aralkyl" refers to an aryl group bonded to a larger entity through an alkyl group, such as benzyl.

The term "substituted aryl" refers to an aryl group substituted by, for example, one to four substituents such as alkyl; substituted alkyl, halo, trifluoromethyl, trifluoromethoxy, hydroxy, alkoxy, cycloalkyloxy, heterocyclooxy, alkanoyl, alkanyloxy, amino, alkylamino, dialkylamino, aralkylamino, cycloalkylamino, heterocycloamino, alkanoylamino, thiol, alkylthio, cycloalkylthio, heterocyclothio, ureido, nitro, cyano, carboxy, carboxyalkyl, carbamyl, alkoxycarbonyl, alkylthio, arylthiono, alkylsulfonyl, sulfonamido, aryloxy and the like. The substituent may be further substituted by one or more members selected from the group consisting of halo, hydroxy, alkyl, alkoxy, aryl, substituted alkyl, substituted aryl and aralkyl.

The term "cycloalkyl" refers to optionally substituted saturated cyclic hydrocarbon ring systems, preferably containing 1 to about 3 rings and 3 to about 7 carbon atoms per ring, which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more of the groups described above as substituents for alkyl groups.

The terms "heterocycle", "heterocyclic" and "heterocyclo" refer to an optionally substituted, unsaturated, partially saturated, or fully saturated, aromatic or nanoaromatic cyclic group, for example, which is a 4- to 7-membered monocyclic, 7-to 11-membered bicyclic, or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperizinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents for the terms "ring system," "heterocycle," "heterocyclic," and "heterocyclo" include one or more substituent groups as described above for substituted alkyl or substituted aryl, and smaller heterocycles, such as, epoxides, aziridines and the like.

The term "alkanoyl" refers to —C(O)-alkyl.

The term "substituted alkanoyl" refers to —C(O)-substituted alkyl.

The term "heteroatoms" shall include oxygen, sulfur and nitrogen.

The compounds represented by formula I form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others as are recognized by those of ordinary skill in the art of pharmaceutical compounding. Such salts are formed by reacting a compound represented by formula I in an equivalent amount of the acid in a medium in which the salt precipitates or in an aqueous medium followed by evaporation.

In addition, zwitterions ("inner salts") can be formed and are included within the term "salts" as used herein. Further, solvates and hydrates of the compounds represented by formula I are also included herein.

The compounds represented by formula I above may exist as multiple optical, geometric, and stereoisomers. While the compounds shown herein are depicted for one optical orientation, included within the present invention are all isomers and mixtures thereof.

It is recognized that the compounds represented by formula I above are microtubule-stabilizing agents. Therefore, they are useful in the treatment of a variety of cancers and other proliferative diseases including, but not limited to, the following:

carcinoma, including that of the bladder, breast, colon, kidney, liver, lung, ovary, pancreas, stomach, cervix, thyroid and skin, including aquamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lympoma, hairy cell lymphoma and Burketts lymphoma;

hematopoietic tumors of meyloid lineage, including acute and chronic myelogenous leukemias and promyelocytic lumekia;

tumors of mesenchymal origin, including fibrosarcoma and rhabdomyosarcoma;

other tumors, including melanoma, seminoma, teratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyosarcoma, and osteosarcoma; and other tumors, including melanoma, xeroderma pigmentosum, keratoacanthoma, seminoma, thyroid follicular cancer and teratocarcincoma.

The foregoing indications are given herein since it cannot be certain which of the named types of tumors, and others as well, may demonstrate resistance to oncology therapy. "Oncology therapy" refers to treatment of cancer or tumors with chemotherapeutic agents that exert a cytotoxic effect in cells. An example of a chemotherapeutic agent is an oncology agent of the taxane family of compounds. It is known, for example, that a considerable number of patients initially responsive to oncology therapy with taxane compounds develop resistance over a course of therapy and that not all cancers respond to treatment with taxane therapy as is the case with virtually all oncology agents. Further, certain diseases, such as cholorectal cancers or melanoma, are known to be innately resistant to taxane therapy.

The subject epothilone compounds are highly potent cytotoxic agents capable of killing cancer cells at low nanometer concentrations and are approximately twice as potent as paclitaxel in inducing tubulin polymerization. More important, the subject compound seem to possess the capacity to retain their antineoplastic activity against human cancers that are naturally insensitive to paclitaxel or have developed resistance to it, both in vitro and in vivo.

Tumors for which the subject epothilone compounds have demonstrated significant antitumor activity include, without intended limitation, the following:

[1] Paclitaxel-resistant—HCT 116VM46 colorectal (multidrug resistant, MDR), Pat-21, breast and Pat-7 ovarian carcinoma (clinical isolates, mechanisms of resistance not fully known), A2780Tax ovarian carcinoma (tubulin mutation);

[2] Paclitaxel-insensitive—Pat-26 human pancreatic carcinoma (clinical isolate) and M5076 murine fibrosarcoma; and

[3] Paclitaxel sensitive—A2780 ovarian, LS 174T and HCT human colon carcinoma.

In addition, the compounds represented by formula I have demonstrated that they are orally efficacious versus preclinical human tumor xenografts grown in immunocompromized mice or rats. Being efficacious upon oral administration is considered a significant advantage of the subject epothilone derivatives.

The present invention thus provides a method of treating a subject, preferably mammals and especially humans, in need of treatment for a tumor that has demonstrated resistance to therapy with the taxane family of oncologic agents, comprising administering to the subject one of the epothilone compounds represented by formula I in an amount effective for such treatment. Other therapeutic agents, such as those described below, may be employed with the subject epothilone compounds in their usual dosages. Such agents may be administered prior to, simultaneously with, or following the subject epothilone compounds.

An effective amount of the epothilone compounds represented by formula I may be determined by one of ordinary skill in the art, and includes exemplary dosage amounts for a human of from about 0.05 to about 200 mg/kg/day. This dosage is typically administered in a single dose, but can be administered in divided doses since the subject compounds are advantageously efficacious via oral administration. The compounds may be administered in a frequent regimen, e.g., every two days for five doses, or intermittently, e.g., every four days for three doses or every eight days for three doses. It will be understood that the specific dose level and frequency of administration for a given subject may be varied and will depend upon a variety of factors, including the subject's age, body weight, general health, sex, diet and the like, the mode of administration if not oral, severity of the condition and the like.

The compounds represented by formula I are administered in pharmaceutical compositions containing an amount thereof effective for cancer therapy, and a pharmaceutically acceptable carrier. Such compositions may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation and/or called for accepted pharmaceutical practice.

The compounds represented by formula I may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, such as by inhalation spray; topically, such as in the form of a cream or ointment; or rectally such as in the form of suppositories; in dosage unit formulations containing non-toxic, pharmaceutically acceptable vehicles or diluents. The subject compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The subject compounds may also be administered liposomally.

Suitable dosage forms for the subject epothilone derivatives include, without intended limitation, a orally effective composition such as a tablet, capsule, solution or suspension containing about 5 to about 500 mg per unit dosage of a compound represented by formula I or a topical form (about 0.01% to about 5% by weight compound represented by formula I, one to five treatments per day). They may be compounded in a conventional manner with a physiologically acceptable vehicle or carrier, excipient, binder, preservative, stabilizer, flavor, etc., or with a topical carrier. The compounds represented by formula I can also be formulated in compositions such as sterile solutions or suspensions for parenteral administration. About 0.1 mg to about 500 mg of a compound represented by formula I may be compounded with a physiologically acceptable vehicle, carrier, excipient, binder preservative, stabilizer, etc., in a unit dosage form as called for by accepted pharmaceutical practice. The amount of active substance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners, or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms that may be used. Exemplary compositions include those formulating the present compound(s) with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g. Gantrez), and agents to control release such as polyacrylic acid copolymer (e.g. Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parentally acceptable diluents or solvents, such as Cremophor® (polyoxyethylated caster oil surfactant), mannitol, 1,3-butanediol, water, Ringer's solution, Lactated Ringer's solution, an isotonic sodium chloride solution, or other suitable dispersion or wetting and suspending agents, including synthetic mono- or diglycerides, and fatty acids, including oleic acid. Exemplary compositions for rectal administration include suppositories which may contain, for example, a suitable non-irritating excipient, such as cocoa butter, synthetic glyceride esters or polyethylene glycols, which are solid at ordinary temperature, but liquefy and/or dissolve in the rectal cavity to release the drug.

The compounds of the invention may be administered either alone or in combination with other chemotherapeutic agents or anti-cancer and cytotoxic agents and/or treatments useful in the treatment of cancer or other proliferative diseases. Especially useful are anti-cancer and cytotoxic drug combinations wherein the second drug chosen acts in a different manner or different phase of the cell, e.g., S phase, than the present compounds represented by formula I which exert their effects at the $G_2$-M phase. Example classes of anti-cancer and cytotoxic agents include, but are not limited to: alkylating agents, such as nitrogen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; and epothilones A–F or their analogs or derivatives; plant-derived products, such as vinca alkaloids, epipodophyllotoxins, and topoisomerase inhibitors; prenyl-protein transferse inhibitors; and miscellaneous agents such as, hydroxyurea, procarbazine, mitotane, hexamethylmelarnine, platinum coordintination complexes such as cisplatin and carboplatin; and other agents used as anti-cancer and cytotoxic agents such as biological response modifiers, growth factors; immune modulators, and monoclonal antibodies. The subject compounds may also be used in conjunction with radiation therapy.

The compounds represented by formula I may also be formulated or co-administered with other therapeutic agents that are selected for their particular usefulness in administering therapies associated with the aforementioned conditions. For example, the compounds of the invention may be formulated with agents to prevent nausea, hypersensitivity, and gastric irritation, such as antiemetics, and $H_1$ and $H_2$ antihistaminics.

The above therapeutic agents, when employed in combination with the compounds of the present invention, may be used in those amounts indicated in the Physicians' Desk Reference (PDR) or as otherwise determined by one of ordinary skill in the art.

The following example is provided, without any intended limitation, to further illustrate the present invention.

EXAMPLE

[1 S-[1R*,3R*(E),7R*,10S*,11R*,12R*,16S*]]-7,11-1-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione (BMS-247550).

For administration to rodents, the subject compound was administered in either 1:9 ethanol/water, or 1:1:8 Cremphor®/ethanol/water. Final dilution for parenteral administration was made with water one hour before administration. Final dilution for oral administration was made with 0.25 M sodium phosphate buffer. Paclitaxel was dissolved in a 50/50 mixture of ethanol and Cremophor® and maintained at 4° C. Final dilution was made immediately prior to injection to prevent undesirable precipitation. Tumor cell lines HCT 116 human carcinoma and HCT116/V/M46 cells were maintained on McCoy's medium and 10% heat-inactivated fetal bovine serum. A2780 human ovarian carcinoma cells and A2780Tax cells were maintained in IMEM and 10% heat-inactivated fetal bovine serum. All other cell lines were maintained in RPM11640 medium with 10% heat-inactivated fetal bovine serum. Cell lines with acquired resistance will be discussed below.

The in vitro cytotoxicity was assessed in tumor cells by a tetrazolium-based colorimetric assay at 492 mm. The cells were seeded 24 h prior to drug addition. The reagents were added following a 72 h incubation with serially diluted test compound. Measurements were taken after a further three hours incubation. The results are expressed as median cytotoxic concentration ($IC_{50}$ values).

Clonogenic cell colony-formation assay: the potency required for the test compound and paclitaxel to kill clonogenic tumor cells (cells that are able to divide indefinitely to form a colony) in vitro was evaluated by a colony formation assay. The concentration needed to kill 90% of clonogenic cancer cells ($IC_{90}$) was determined.

Tubulin polymerization assay: the potency required for the test compound and paclitaxel to polymerize tubulin isolated from calf brain was evaluated by published techniques. The effective concentration ($EC_{0.01}$) was defined as the interpolated concentration capable of inducing an initial slope of optical density (OD) of 0.01 OD/minute rate and is calculated using the formula: $EC_{0.01}$=concentration/slope. $EC_{0.01}$ values are expressed as the mean with standard deviation obtained from 3 different concentrations.

In Vivo Antitumor Testing: The following human tumors were used: ovarian carcinoma A2780, A2780Tax and Pat-7 (established from an ovarian tumor biopsy from a patient who had developed resistance to paclitaxel); HCT116, HCT116/VM46 and LS174T colon carcinomas, Pat-21 breast carcinoma, and Pat-26 pancreatic carcinoma (from a liver metastasis biopsy). Pat-7, Pat-21 and Pat-26 xenografts were established initially from primary tumor biopsies directly as xenotransplants grown in whole-body irradiated nude mice without any intervening in vitro cell culturing steps. The innately paclitaxel-insensitive murine fibrosarcoma M5076 was also employed. The human tumor xenografts were maintained in Balb/c nu/nu nude mice. M5076 was maintained in C57BL/6 mice. Tumors were propagated as subcutaneous transplants in the appropriate mouse strain using tumor fragments obtains from donor mice. Tumor passage occupied biweekly for murine tumors and approximately every two to eight weeks for the various human tumor lines. With regard to efficacy testing, M5076 tumors were implanted in (C57B1/6×DBA/2)F1 hybrid mice, and human tumors were implanted in nude mice. All tumor implants for efficacy testing were subcutaneous (sc).

The required number of animals needed to detect a meaningful response (6–8) were pooled at the start of the experiment and each was given a subcutaneous implant of a tumor fragment (~50 mg) with a 13-gauge trocar. For treatment of early-stage tumors, the animals were again pooled before distribution to the various treatment and control groups. For treatment of animals with advanced-stage disease, tumors were allowed to grow to the predetermined size window (tumors outside the range were excluded) and animals were evenly distributed to various treatment and control groups. Treatment of each animal was based on individual body weight. Treated animals were checked daily for treatment related toxicity/mortality. Each group of animals was weighed before the inhalation of treatment (Wt1) and then again following the last treatment dose (Wt2). The difference in body weight (Wt2–Wt1) provided a measure of treatment-related toxicity.

Tumor response was determined by measurement of tumors with a caliper twice a week until the tumors reached a predetermined "target" size of 0.5 or 1.0 g. Tumor weights (mg) were estimated from the formula:

$$\text{Tumor weight}=(\text{length}\times\text{weight})\div 2$$

The maximum tolerated dose (MTD) is defined as the dose level immediately above which excessive toxicity (i.e. more than one death) occurred. The MTD was frequently equivalent to the optimal dose (OD). Activity is described at the OD. Treated mice expiring prior to having their tumors reach target size were considered to have expired from drug toxicity. No control mice expired bearing tumors less than target size. Treatment groups with more than one death caused by drug toxicity were considered to have had excessively toxic treatments and their data were not included in the evaluation of a compound's antitumor efficacy.

Tumor response end-point was expressed in terms of tumor growth delay (T–C value), defined as the difference in time (days) required for the treated tumors (T) to reach a predetermined target size compared to those of the control group (C). A tumor is defined as "cured" when there is no detectable disease at the time of study termination; the interval between study termination and the end of drug treatment always exceeded 10 times the tumor volume doubling time. Group sizes typically consisted of eight mice in all treatment and control groups. Statistical analyses of response data were carried out using the Gehan's generalized Wilcoxon test.

Cytotoxicity Against Cancer Cells in vitro: As shown in FIG. 1, the results demonstrate the test compound has a broad spectrum of activity against a panel of tumor cell lines in vitro. Of the 21 cells lines tested, the $IC_{50}$ values were in the range of 1.4–34.5 nM. Significantly, the test compound appeared to overcome to a large extent the two main mechanisms of resistance to paclitaxel, viz. MDR resistance due to P-glycoprotein overexpression (exemplified by HCT116/VM46) and β-tubulin mutation (exemplified by A2780Tax). The test compound and paclitaxel were similarly potent in killing clonogenic cells in the two sensitive tumor cell lines (HCT116 and A2780). However, as shown in FIG. 2, against the three cell lines that had developed resistance to paclitaxel (HCT116/VM46, A2780Tax and Pat-7), the test compound performed far better than paclitaxel, almost completely retaining its cytotoxic potency against these resistant cell lines as compared to the sensitive lines.

Mechanism of Cytotoxicity—Tubulin Polymerization: The cytotoxic activities of the epothilones, like those of the taxanes, have been linked to stabilization of microtubules, which results in mitotic arrest at the G2/M transition. In this regard, the potency of the test compound was about 2.5-fold more potent than paclitaxel.

Mechanism of Cytotoxicity—Effects on Cell Cycle Progression: Similar to paclitaxel, the test compound blocks cells in the mitotic phase of the cell division cycle. Moreover, the concentration of the test compound needed to arrest cells in mitosis, as measured by flow cytometry, corresponds well to the concentration required to kill cells over the same treatment duration. Thus, as shown in FIG. 3, the test compound at a concentration close to the $IC_{90}$ value (about 7.5 nM, clonogenic cytotoxicity assay) almost completely blocks cells in mitosis as early as 8 hours following the initiation of drug exposure.

Antitumor Activity by Parenteral Administration: The test compound was evaluated in a panel of eight human and murine tumor models, some of which were chosen because of their known, well-characterized resistance to paclitaxel. The tumor model characteristics are shown in Table 1 below. In addition, three paclitaxel-sensitive models were included in order to gain a full assessment of the spectrum of antitumor activity of the test compound.

TABLE 1

| Tumor | Histology | Source | Paclitaxel Sensitivity | Resistance Mechanism(s) |
|---|---|---|---|---|
| Human | | | | |
| Pat-26 | Pancreatic | Biopsy | Insensitive | Unknown |
| Pat-7 | Ovarian | Biopsy | Resistant[1] | MDR[2], MRP[3] |
| A2780Tax | Ovarian | Cell line | Resistant | Tubulin mutation |
| HCT116/VM46 | Colon | Cell line | Resistant | MDR |
| Pat-21 | Breast | Biopsy | Resistant[1] | Unknown |

TABLE 1-continued

| Tumor | Histology | Source | Paclitaxel Sensitivity | Resistance Mechanism(s) |
|---|---|---|---|---|
| A2780 | Ovarian | Cell line | Sensitive | NA |
| HCT116 | Colon | Cell line | Sensitive | NA |
| LS174T | Colon | Cell line | Sensitive | NA |
| Murine | | | | |
| M5076 | Fibrosarcoma | Cell line | Insensitive | Unknown, Non-MDR |

[1]Clinical resistance to Taxol ®
[2]MDR = multidrug resistance due to P-glycoprotein overexpression
[3]MRP = multidrug resistance related protein Antitumor Activity by Oral Route of Administration: Since the test compound is more stable at neutral pH than at low pH, the evaluation thereof by oral administration (PO) utilized a pH-buffering vehicle (0.25M potassium phosphate, pH 8.0). Using a every 2 days×5 schedule, the test compound was highly active orally against the Pat-7 human ovarian carcinoma model. In two separate experiments, orally administered test compound yielded 3.1 and 2.5 LCKs at its MTD. In comparison, concomitantly tested IV paclitaxel produced 1.3 and 1.2 LCK, respectively, at its optimal dose and schedule. Paclitaxel is typically inactive when administered by the oral route.

From the foregoing in vitro experimental evidence, it can be seen that the test compound retains its antineoplastic activity in cancer cells that have developed resistance to paclitaxel, whether through overexpression of the MDR P-glycoprotein or tubulin mutation. From the in vivo evidence, the test compound has clearly demonstrated antitumor activity superior to paclitaxel in both paclitaxel-resistant and sensitive tumors, and the murine fibrosarcoma M5076. The test compound was more efficacious than paclitaxel in all five paclitaxel-resistant tumors evaluated in this study (four human and one murine); viz. the clinically-derived paclitaxel resistant Pat-7 ovarian carcinoma; the A2780Tax ovarian carcinoma that is resistant to paclitaxel because of tubulin mutations; the HCT116/VM46 multidrug resistant (MDR) colon carcinoma, the clinically-derived paclitaxel-resistant Pat-21 breast carcinoma; and the murine fibrosarcoma M5076. Against three paclitaxel-sensitive human tumor xenografts, viz. A2780 human ovarians carcinoma; HCT116 and LS 174T human colon carcinoma, the test compound produced antitumor activity equivalent to paclitaxel.

A further advantage of the test compound over the prototypical taxanes is its efficacy by oral administration, producing antitumor activity when given orally that is equivalent to that produced by IV drug administration in two different human tumor xenografts.

What is claimed is:

[1. A method for treating a tumor in a mammal, said tumor having demonstrated resistance to oncology therapy, comprising administering to said mammal an effective amount of a composition comprising a pharmaceutically acceptable carrier and an epothilone compound of formula:

I

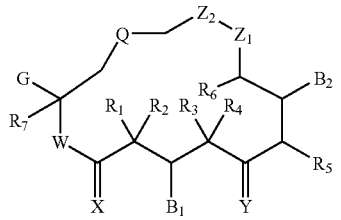

wherein:

Q is selected from the group consisting of

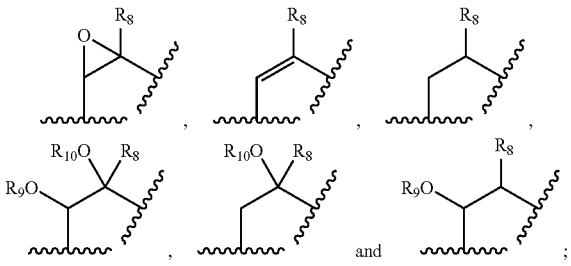

G is selected from the group consisting of alkyl, substituted alkyl, aryl, substituted aryl, heterocyclo,

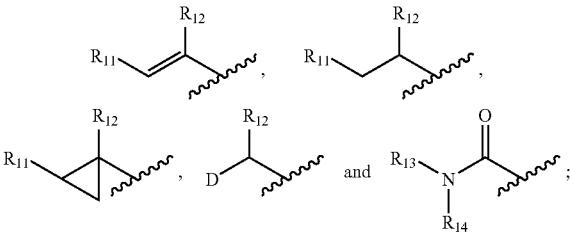

W is O or $NR_{15}$;

X is O or H, H;

Y is selected from the group consisting of O; H, $OR_{16}$; $OR_{17}$, $OR_{17}$; $NOR_{18}$; H, $NHOR_{19}$; H, $NR_{20}R_{21}$; H, H; and $CHR_{22}$; wherein $OR_{17}$, $OR_{17}$ can be a cyclic ketal;

each $Z_1$ and $Z_2$ is, independently, selected from the group consisting of $CH_2$, O, $NR_{23}$, S, and $SO_2$, wherein only one of $Z_1$ and $Z_2$ can be a heteroatom;

each $B_1$ and $B_2$ is, independently, selected from the group consisting of $OR_{24}$, $OCOR_{25}$, and O—C(═O)—$NR_{26}R_{27}$, and when $B_1$ is H and Y is OH, H, they can form a six-membered ring ketal or acetal;

D is selected from the group consisting of $NR_{28}R_{29}$, $NR_{30}COR_{31}$ and saturated heterocycle;

each $R_1$, $R_2$, $R_3$, $R_4$, $R_5$, $R_6$, $R_7$, $R_{13}$, $R_{14}$, $R_{18}$, $R_{19}$, $R_{20}$, $R_{21}$, $R_{22}$, $R_{26}$ and $R_{27}$ is, independently, selected from the group consisting of H, alkyl, substituted alkyl, and aryl, and when $R_1$ and $R_2$ are alkyl can be joined to form a cycloalkyl, and when $R_3$ and $R_4$ are alkyl can be joined to form a cycloalkyl;

each $R_9$, $R_{10}$, $R_{16}$, $R_{17}$, $R_{24}$, $R_{25}$ and $R_{31}$ is, independently, selected from the group consisting of H, alkyl, and substituted alkyl;

each $R_8$, $R_{11}$, $R_{12}$, $R_{28}$, $R_{30}$, $R_{32}$, and $R_{33}$ is, independently, selected from the group consisting of H, alkyl, substituted alkyl, aryl, substituted aryl, cycloalkyl and heterocyclo; and each $R_{15}$, $R_{23}$ and $R_{29}$ is, independently, selected from the group consisting of H, alkyl, substituted alkyl, aryl, substituted aryl, cycloalkyl, heterocyclo, $R_{32}C{=}O$, $R_{33}SO_2$, hydroxy, O-alkyl or O-substituted alkyl;

and pharmaceutically acceptable salts thereof and any hydrates, solvates or geometric, optical and stereoisomers thereof, with the proviso that compounds wherein W and X are both O; $R_1$, $R_2$ and $R_7$ are H; $R_3$ $R_4$ and $R_6$ are methyl; $R_8$ is H or methyl; $Z_1$ and $Z_2$ are $CH_2$; G is 1-methyl-2-(substituted-4-thiazolyl)ethenyl; and Q is as defined above, are excluded.]

[2. The method of claim 1 wherein Q is

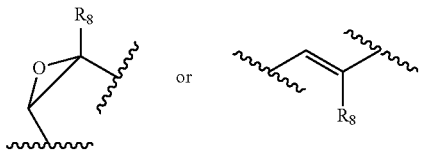

X is O; Y is O; each $Z_1$ and $Z_2$ is, independently, $CH_2$; and W is $NR_{15}$.]

[3. The method of claim 1 wherein said epothilone compound is selected from the group consisting of

[1S-[1R*,3R*(E), 7R*,10S*,11R*,12R*,16S*]]-7,11-dihydroxy-8,8,10,12,16-pentamethyl-3-[1-methyl-2-(2-methyl-4-thiazolyl)ethenyl]-4,13,17-trioxabicyclo[14.1.0]heptadecane-5,9-dione;

[1S-[1R*,3R*(E),7R*,10S*,11R*,12R*,16S*]]-7,11-dihydroxy-8,8,10,12-tetrametlnrl-3-[1-methyl-2-(2-methyl-4-thiazolyl)ethenyl]-4,13,17-trioxabicyclo[14.1.0]heptadecane-5,9-dione;

[4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-1,10-dioxa-13-cyclohexadecene-2,6-dione;

[4S-[4R*,7S*,8R*,9R*,15R*(E)]]-4,8-dihydroxy-5,5,7,9-tetramethyl-16-[1-methyl-2-(2-methyl-4-thiazolyl)ethenyl]-1,10-dioxa-13-cyclohexadecene-2,6-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4,14,17-trioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-4,14,17-trioxabicyclo[14.1.0]heptadecane-5,9-dione;

[4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-1,11-dioxa-13-cyclohexadecene-2,6-dione;

[4S-[4R*,7S*,8R*,9R*,15R*(E)]]-4,8-dihydroxy-5,5,7,9-tetramethyl-16-[1-methyl-2-(2-methyl-4-thiazolyl)ethenyl]-1,11-dioxa-13-cyclohexadecene-2,6-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4,17-dioxabicyclo[14.1.0]heptadecane-9-one;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-4,17-dioxabicyclo[14.1.0]heptadecane-9-one;

[1S-[1R*,3R*(E),7R*,10S*,11R*,12R*,16S*]]-7,11-dihydroxy-3,8,8,10,12,16-hexamethyl-3-[1-methyl-2-(2-methyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-dihydroxy-3,8,8,10,12-pentamethyl-3-[1-methyl-2-(2-methyl-4-thiazolyl)ethenyl]-4,17-dioxabicyclo[14.1.0]heptadecane-5,9-dione;

[4S-[4R*,7S*,8R*,9R*,15R*(E)]]-4,8-dihydroxy-5,5,7,9,13,16-hexamethyl-16-[1-methyl-2-(2-methyl-4-thiazolyl)ethenyl]-1-oxa-13-cyclohexadecene-2,6-dione;

[4S-[4R*,7S*,8R*,9R*,15R*(E)]]-4,8-dihydroxy-5,5,7,9,16-pentamethyl-16-[1-methyl-2-(2-methyl-4-thiazolyl)ethenyl]-1-oxa-13-cyclohexadecene-2,6-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-dihydroxy-6,8,8,10,12-pentamethyl-3-[1-methyl-2-(2-methyl-4-thiazolyl)ethenyl]-4,17-dioxabicyclo[14.1.0]heptadecane-5,9-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-4-aza-17-oxabicycllo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-4-aza-17oxabicyclo[14.1.0]heptadecane-5,9-dione;

[4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-1-aza-13-cyclohexadecene-2,6-dione;

[4S-[4R*,7S*,8R*,9R*,15R*(E)]]-4,8-dihydroxy-5,5,7,9-tetramethyl-16-[1-methyl-2-(2-methyl-4-thiazolyl)ethenyl]-1-aza-13-cyclohexadecene-2,6-dione;

[1S-1R*,3R*(E),7R*,10S*,11R*,12R*,16S*]]-7,11-dihydroxy-4,8,8,10,12,16-hexamethyl-3-[1-methyl-2-(2-methyl-4-thiazolyl)ethenyl]-4-aza-17-oxabicyclo[14.1.0]heptadecane-5,9-dione;

[1S-[1R*,3R*(E),7R*,10S*,11R*,12R*,16S*]]-7,11-dihydroxy-4,8,8,10,12-pentamethyl-3-[1-methyl-2-(2-methyl-4-thiazolyl)ethenyl]-4-aza-17-oxabicyclo[14.1.0]heptadecane-5,9-dione;

[4S-[4R*,7S*,8R*,9R*,15R*(E)]]-4,8-dihydroxy-1,5,5,7,9,13-hexamethyl-16-[1-methyl-2-(2-methyl-4-thiazolyl)ethenyl]-1-aza-13-cyclohexadecene-2,6-dione;

[4S-[4R*,7S*,8R*,9R*,15R*(E)]]-4,8-dihydroxy-1,5,5,7,9-pentamethyl-16-[1-methyl-2-(2-methyl-4-thiazolyl)ethenyl]-1-aza-13-cyclohexadecene-2,6-dione;

[1S-[1R*,3R*(E),7R*,10S*,11R*,12R*,16S*]]-7,11-dihdyroxy-8,8,10,12,16-pentamethyl-3-[1-methyl-2-(2-methyl-4-thiazolyl)ethenyl]-13-aza-4,17dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-13-aza-4,17dioxabicyclo[14.1.0]heptadecane-5,9-dione;

[4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-10-aza-1-oxa-13-cyclohexadecene-2,6-dione;

[4S-[4R*,7S*,8R*,9R*,15R*(E)]]-4,8-dihydroxy-5,5,7,9-tetramethyl-16-[1-methyl-2-(2-methyl-4-thiazolyl)ethenyl]-10-aza-1-oxa-13-cyclohexadecene-2,6-dione;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)ethenyl]-14-aza-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)ethenyl]-14-aza-4,17-dioxabicyclo[14.1.0]heptanedecane-5,9-dione;

[4S-[4R*,7S*,8R*,9R*,15R*(E)]]-4,8-dihydroxy-5,5,7,9,13-pentamethyl-16-[1-methyl-2-(2-methyl-4-thiazolyl)ethenyl]-11-aza-1-oxa-13-cyclohexadecene-2,6dione;

[4S-[4R*,7S*,8R*,9R*,15R*(E)]]-4,8-dihydroxy-5,5,7,9-tetramethyl-16-[1-methyl-2-(2-methyl-4-thiazolyl)ethenyl]-11-aza-1-oxa-13-cyclohexadecene-2,6-dione;

[1S-[1R*,3R*,7R*,10S*,11R*,12R*,16S*]]-N-phenyl-7,11-dihydroxy-8,8,10,12,16-pentamethyl-5,9-dioxo-4,17-dioxabicyclo[14.1.0]heptadecane-3-carboxamide;

[1S-[1R*,3R*,7R*,10S*,11R*,12R*,16S*]]-N-phenyl-7,11-dihydroxy-8,8,10,12-tetramethyl-5,9-dioxo-4,17-dioxabicyclo[14.1.0]heptadecane-3-carboxamide;

[4S-[4R*,7S*,8R*,9R*,15R*]]-N-phenyl-4,8-dihydroxy-5,5,7,9,13-pentamethyl-2,6-dioxo-1-oxa-13-cyclohexadecene-16-carboxamide;

[4S-[4R*,7S*,8R*,9R*,15R*]]-N-phenyl-4,8-dihydroxy-5,5,7,9-tetramethyl-2,6-dioxo-1-oxa-13-cyclohexadecene-16-carboxamide;

[1S-[1R*,3R*(E),7R*,10S*,11R*,12R*,16S*]]-7,11-dihydroxy-8,8,10,12,16-pentamethyl-3-[1-methyl-2-(2-methyl-4-thiazolyl)cyclopropyl]-4,17-dioxabicyclo[14.1.0]heptadecane-5,9-dione;

[1S-[1R*,3R*(E),7R*,10S*,11R*,12R*,16S*]]-7,11-dihydroxy-8,8,10,12-tetramethyl-3-[1-methyl-2-(2-methyl-4-thiazolyl)cyclopropyl]-4,17-dioxabicyclo[14.1.0]heptadecane-5,9-dione; and

[4S-[4R*,7S*,8R*,9R*,15R*(E)]]-4,8-dihydroxy-5,5,7,9,13-pentamethyl-16-[1-methyl-2-(2-hydroxymethyl-4-thiazolyl)ethenyl]-1-aza-13(Z)-cyclohexadecene-2,6-dione;

and pharmaceutically acceptable salts, solvates and hydrates thereof.]

[4. The method of claim 1 wherein said epothilone compound is of formula:

[

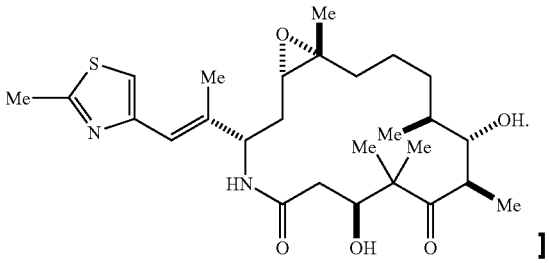

]

]

[5. The method of claim 1 wherein said mammal is a human.]

[6. The method of claim 1 wherein the composition containing said epothilone compound is administered parenterally.]

[7. The method of claim 6 wherein said epothilone compound is of formula:

[

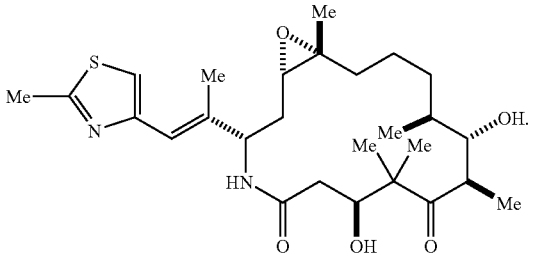

]

]

[8. The method of claim 1 wherein the composition containing said epothilone compound is administered orally.]

[9. The method of claim 8 wherein said epothilone compound is of formula:

[

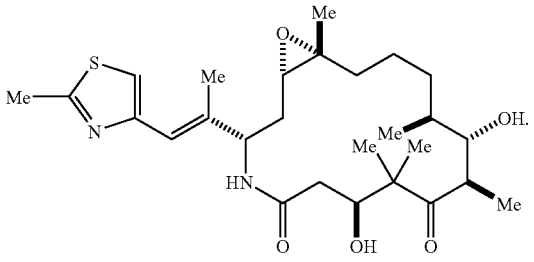

]

]

[10. The method of claim 1 wherein said tumor was initially not responsive to oncology therapy.]

[11. The method of claim 1 wherein said tumor was initially responsive to oncology therapy, but developed resistance thereto during the course of treatment.]

[12. The method of claim 1 wherein said compound is administered simultaneously or sequentially with a chemotherapeutic agent useful in the treatment of cancer or other proliferative diseases.]

[13. The method of claim 1 wherein the oncology therapy is a taxane.]

[14. The method of claim 1 wherein the oncology therapy is paclitaxel.]

[15. The method of claim 1 wherein the tumor is of the bladder, breast, colon, kidney, liver, lung, ovary, pancreas, stomach, cervix, thyroid or skin.]

*16. A method for treating a tumor in a mammal, said tumor being resistant to oncology therapy with a taxane, comprising administering to said mammal an effective amount of a composition comprising a pharmaceutically acceptable carrier and a compound having the formula,*

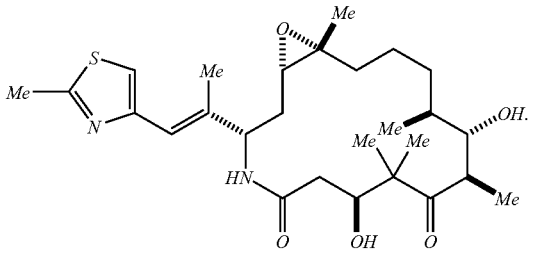

*17. The method of claim 16 wherein said mammal is a human.*

*18. The method of claim 17 wherein said tumor was initially not responsive to taxane therapy.*

*19. The method of claim 17, wherein said tumor was initially responsive to taxane therapy, but developed resistance thereto during the course of treatment.*

*20. The method of claim 17, wherein said tumor is innately resistant to taxane therapy.*

*21. The method of claim 17, wherein the taxane is paclitaxel.*

*22. The method of claim 17 wherein the tumor is of the bladder, breast, colon, kidney, liver, lung, ovary, pancreas, stomach, cervix, thyroid or skin.*

*23. The method of claim 22, wherein the tumor is of the breast.*

*24. The method of claim 22, wherein the tumor is of the pancreas.*

*25. The method of claim 23, wherein the oncology therapy is paclitaxel.*

*26. The method of claim 23 wherein said tumor was initially not responsive to taxane therapy.*

*27. The method of claim 23 wherein said tumor was initially responsive to taxane therapy, but developed resistance thereto during the course of treatment.*

*28. The method of claim 23, wherein said tumor is innately resistant to taxane therapy.*

* * * * *